United States Patent
Borck et al.

(10) Patent No.: US 7,939,146 B2
(45) Date of Patent: May 10, 2011

(54) MARKER COMPOSITE FOR MEDICAL IMPLANTS

(75) Inventors: Alexander Borck, Aurachtal (DE); Ellen Korzuschnik, Hetzles (DE); Claus Harder, Uttenreuth (DE); Heinz Mueller, Erlangen (DE)

(73) Assignee: Biotronik VI Patent AG, Baar (CH)

( * ) Notice: Subject to any disclaimer, the term of this patent is extended or adjusted under 35 U.S.C. 154(b) by 870 days.

(21) Appl. No.: 11/834,711

(22) Filed: Aug. 7, 2007

(65) Prior Publication Data

US 2008/0033533 A1 Feb. 7, 2008

(30) Foreign Application Priority Data

Aug. 7, 2006 (DE) .................... 10 2006 038 233

(51) Int. Cl.
*B32B 1/00* (2006.01)
*B32B 5/16* (2006.01)
*A61F 2/02* (2006.01)
*C04B 35/66* (2006.01)

(52) U.S. Cl. .... 428/34.1; 428/323; 428/332; 623/11.11; 252/478

(58) Field of Classification Search ................. 428/34.1, 428/35.2, 35.3–35.9, 36.1, 36.2, 36.4, 36.6, 428/36.7–36.92, 323, 328, 332; 604/19, 604/93.01, 96.01, 100.01, 101.01, 103.1; 623/1.1, 1.11, 1.34–1.54, 11.11–23.76; 252/478, 252/600
See application file for complete search history.

(56) References Cited

U.S. PATENT DOCUMENTS

| 5,234,695 | A | * | 8/1993 | Hobbs et al. ............... 424/489 |
| 5,395,629 | A | * | 3/1995 | Bertoli et al. ................ 426/35 |
| 6,077,880 | A | | 6/2000 | Castillo et al. |
| 7,481,798 | B2 | * | 1/2009 | Rioux et al. ................. 604/256 |
| 7,704,275 | B2 | * | 4/2010 | Schmid et al. ............. 623/1.16 |
| 2002/0058057 | A1 | | 5/2002 | Kaplan |
| 2006/0188545 | A1 | * | 8/2006 | Hadba ......................... 424/426 |
| 2006/0251710 | A1 | * | 11/2006 | Kwon et al. ................. 424/450 |

FOREIGN PATENT DOCUMENTS

| DE | 10361942 A1 | 7/2005 |
| EP | 0824900 A2 | 2/1998 |
| EP | 0894503 A2 | 2/1999 |
| EP | 1270023 A2 | 1/2003 |
| WO | 03039612 A1 | 5/2003 |
| WO | 2004/043474 A2 | 5/2004 |

OTHER PUBLICATIONS

Search Report for European Patent Application No. 07013432.5; Apr. 11, 2008.
Search Report for German Patent Application No. 10 2006 038 233.1; Apr. 25, 2007.

* cited by examiner

*Primary Examiner* — Walter B Aughenbaugh
(74) *Attorney, Agent, or Firm* — Jason A. Bernstein; Barnes & Thornburg LLP

(57) ABSTRACT

An x-ray marker for medical implants made of a biocorrodible metallic material, wherein the x-ray marker composite includes 1-40 weight parts of a carrier matrix having a melting point greater than or equal to 43° C., which comprises 90 weight-percent or more at least one triglyceride; and 60-99 weight parts of a radiopaque marker component which is embedded in the carrier matrix.

8 Claims, No Drawings

MARKER COMPOSITE FOR MEDICAL IMPLANTS

PRIORITY CLAIM

This patent application claims priority to German Patent Application No. 10 2006 038 233.1, filed Aug. 7, 2006, the disclosure of which is incorporated herein by reference in its entirety.

FIELD

The present disclosure relates to a marker composite for medical implants made of a biocorrodible metallic material and a medical implant which is coated or filled with a marker composite made of a biocorrodible metallic material.

BACKGROUND

Implants have found applications in modern medical technology in manifold embodiments. For example, implants are used for supporting vessels, hollow organs, and duct systems (endovascular implants); for attaching and temporarily fixing tissue implants and tissue transplants; and for orthopedic purposes, for example, as nails, plates, or screws.

For radiological intraoperative and postoperative position monitoring, implants are provided with a marker if they do not already comprise a sufficiently radiopaque material. The x-ray visibility of the marker is a function of the dimensions and the x-ray absorption coefficient. The x-ray absorption coefficient is, in turn, a function of the energy range of the x-ray radiation. In the medical field, this is typically from 60 to 120 keV; for coronary use, a range of from 80 to 100 keV is typically employed. The x-ray absorption coefficient typically becomes larger with rising atomic number in the periodic table and the rising density of the material. The presence of the marker should not restrict the functionality of the implant or be a starting point for inflammation or rejection reactions of the body. Typically, for example, noble metals, such as gold, platinum and the like, are used as marker materials.

The markers are provided (i) as solid material, e.g., in the form of a coating, a strip, an inlay, or a molded body permanently bonded to the implant, or (ii) as powder embedded in a carrier matrix, in the form of a coating or as a filler material for a cavity in the implant. Variant (ii) may be implemented especially simply in production technology; a castable or sprayable mixture made of the radiopaque marker component and the material acting as a carrier matrix, possibly with a solvent added, is processed.

After fulfilling the therapeutic purpose, implants are removed operatively, for example, if this is still possible, because the implants remaining permanently in the body may result in inflammation or rejection reactions. An alternative to an operation is the use of biocorrodible materials for the implant. The number of biocorrodible materials based on polymers or metals is continuously growing. Thus, inter alia, biocorrodible metal alloys of the elements magnesium, iron, and tungsten are known. For example, European Patent Application No. 1 270 023 describes a magnesium alloy which is suitable for endovascular and orthopedic implants.

The biocorrodible metal alloys and polymers for medical implants known in the art have only slight x-ray visibility in the energy range of 80-100 keV, which is used for medical technology. However, x-ray diagnosis is an important instrument precisely for postoperative monitoring of the healing progress or for checking minimally invasive interventions. Thus, for example, stents have been placed in the coronary arteries during acute myocardial infarction treatment for some years. The stent is positioned in the area of the lesion of the coronary vascular wall and prevents obstruction of the vascular wall after expansion. The procedure of positioning and expanding the stent must be continuously monitored by the cardiologist during the procedure.

In implants made of biocorrodible metallic materials based on magnesium, iron, or tungsten, there are increased requirements for the marker material which include:

- the marker is not to be detached early from the main body of the implant by the corrosive processes, to avoid fragmentation and thus the danger of embolization;
- the marker is to have sufficient x-ray density even at low material thicknesses, and
- the marker material is to have no or, at most, a slight influence on the degradation of the main body.

German Patent Application No. 103 61 942 A1 describes a radiopaque marker for medical implants, which contains 10 to 90 weight-percent of a biocorrodible base component, in particular, from the group of elements consisting of magnesium, iron, and zinc. Furthermore, the marker contains 10 to 90 weight-percent of one or more radiopaque elements from the group consisting of I, Au, Ta, Y, Nb, Mo, Ru, Rh, Ba, La, Ce, Pr, Nd, Sm, Eu, Gd, Tb, Dy, Ho, Er, Tm, Yb, Lu, Hf, Ta, W, Re, Os, Bi, combinations thereof and the like as a marker component. The marker described is suitable in principle for use in biocorrodible implants, in particular, those made of biocorrodible magnesium alloys.

However, the special problem arises upon the use of markers made of metallic materials on biocorrodible metallic main bodies that, because of electrochemical interactions between the two metallic materials, the degradation of the main body is altered in a contact area between marker and main body, i.e., the degradation is typically accelerated.

SUMMARY

The present disclosure provides several exemplary embodiments of the present invention.

One aspect of the present disclosure provides a marker composite for medical implants made of a biocorrodible metallic material, the marker composite comprising (a) 1-40 weight parts of a carrier matrix having a melting point greater than or equal to 43° C., which comprises 90 weight-percent or more triglycerides; and (b) 60-99 weight parts of a radiopaque marker component, which is embedded in the carrier matrix.

Another aspect of the present disclosure provides a medical implant coated and/or filled with a marker composite made of a biocorrodible metallic material, comprising (a) 1-40 weight parts of a carrier matrix having a melting point greater than or equal to 43° C., which comprises 90 weight-percent or more triglycerides; and (b) 60-99 weight parts of a radiopaque marker component, which is embedded in the carrier matrix.

A further aspect of the present disclosure provides a medical implant, coated and/or filled with a marker made of a biocorrodible magnesium alloy, comprising (a) 1-40 weight parts of a carrier matrix having a melting point greater than or equal to 43° C., which comprises 90 weight-percent or more triglycerides; and (b) 60-99 weight parts of a radiopaque marker component, which is embedded in the carrier matrix.

An additional aspect of the present disclosure provides a medical implant, coated and/or filled with a marker composite made of a biocorrodible metallic material, comprising (a) 1-40 weight parts of a carrier matrix having a melting point greater than or equal to 43° C., which comprises 90 weight-percent or more triglycerides; and (b) 60-99 weight parts of a radiopaque marker component, which is embedded in the carrier matrix; wherein the carrier matrix comprises 90 weight-percent or more of a hydrogenated soybean oil having a proportion of palmitic acid in the fatty acids of the triglyceride in the range from 9-16 weight-percent and a proportion of stearic acid in the fatty acids of the triglyceride in the range from 79-89 weight-percent.

DETAILED DESCRIPTION

Surprisingly, it has been shown that the use of a triglyceride matrix is especially advantageous for receiving radiopaque marker components; the material is identical to natural material or of natural origin and is, therefore, highly biocompatible, biologically degradable, has good adhesion capability on metallic surfaces, may be acquired cost-effectively, and is easy to handle in processing technology.

For purposes of the present disclosure, the term triglycerides (also triacylglycerides, triacylglycerols) is a collective term for esters of glycerol (glycerides), in which all three hydroxy groups are esterified by fatty acids. The triglycerides are of natural origin or so-called structured triglycerides. For purposes of the present disclosure, structured triglycerides are understood as triglycerides whose natural distribution of the fatty acid residues on the primary positions of the glycerol framework (sn-1, sn-2, sn-3) has been intentionally altered by chemical, biochemical, plant-agricultural, or genetic measures to provide fats with specific food-technology, biochemical, or physiological properties. Triglycerides are hydrophobic and polymorphic, i.e., the triglycerides crystallize in various modifications, which are referred to as $\gamma$, $\alpha$, $\beta'$, or $\beta$. The $\beta$ form is the most stable. The melting point of the triglycerides is a function of the fatty acid composition and the position in the triglyceride molecule. The presence of cis-unsaturated fatty acids typically lowers the melting temperature.

The triglycerides according to the present disclosure are distinguished in that they have a melting point of the $\beta$ form of 43° C. or more. This melting point ensures that the carrier matrix remains solid even in the event of a high fever of the patient, and thus the danger of an embolization induced by loss of the marker may be counteracted. The melting point of the $\beta$ form is preferably in the temperature range of from 43° C. to 100° C. Triglycerides having a melting point of the $\beta$ form above 100° C. may only be handled in processing technology with difficulty and have less adhesion capability than triglycerides having a lower a melting point.

According to one exemplary embodiment, the carrier matrix comprises 90 weight-percent or more of a hydrogenated soybean oil having a proportion of palmitic acid in the fatty acids of the triglyceride in the range from 9 to 16 weight-percent and a proportion of stearic acid in the fatty acids of the triglyceride in the range from 79 to 89 weight-percent. It has been shown that a carrier matrix of the cited composition permits especially easy processing and has a high adhesion capability. In addition, the material has extraordinarily high biocompatibility. The carrier matrix preferably contains 0.1 to 20 weight-percent, more preferably 0.5 to 20 weight-percent, tocopherol as an additive which lowers the viscosity of the carrier matrix. The processing is thus simplified.

All typical materials cited in connection with implants, such as metals or inorganic salts, may be used as radiopaque marker components. The marker component is provided in a carrier matrix in dissolved or suspended form. The marker component is preferably a metal powder, in particular, having a mean particle size greater than or equal to 3 µm. The metal powder is preferably an element selected from the group consisting of gold, iridium, platinum, and tantalum. The use of finely powdered marker components simplifies the processing and application of the marker composite to the implant and/or introducing the marker composite into a cavity of the implant. The carrier matrix reduces a contact surface between the metallic marker components in the main body of the implant so that undesired interactions in regard to the corrosion behavior are avoided or at least reduced. The area of the implant which is to carry the marker is preferably coated with a small quantity of the triglyceride carrier matrix before application of the marker.

The biocorrodible metallic material is preferably a biocorrodible alloy selected from the group consisting of magnesium, iron, and tungsten; in particular, the biocorrodible metallic material is preferably a magnesium alloy. For purposes of the present disclosure, an alloy is a metallic structure whose main component is magnesium, iron, or tungsten. The main component is the alloy component whose weight proportion in the alloy is highest. A proportion of the main component is preferably more than 50 weight-percent, in particular more than 70 weight-percent.

If the material is a magnesium alloy, the material preferably contains yttrium and further rare earth metals, because an alloy of this type is distinguished on the basis of the physiochemical properties and the high biocompatibility, in particular, the degradation products.

A magnesium alloy of the composition of rare earth metals 5.2-9.9 weight-percent, yttrium 3.7-5.5 weight-percent, and the remainder less than 1 weight-percent is especially preferable, magnesium making up the proportion of the alloy to 100 weight-percent. This magnesium alloy has already confirmed its special suitability experimentally and in initial clinical trials, i.e., the magnesium alloy displays a high biocompatibility, favorable processing properties, good mechanical characteristics, and corrosion behavior adequate for the intended uses. For purposes of the present disclosure, the collective term "rare earth metals" includes scandium (21), yttrium (39), lanthanum (57) and the 14 elements following lanthanum (57), namely cerium (58), praseodymium (59), neodymium (60), promethium (61), samarium (62), europium (63), gadolinium (64), terbium (65), dysprosium (66), holmium (67), erbium (68), thulium (69), ytterbium (70), and lutetium (71).

The alloys of the elements magnesium, iron, or tungsten are to be selected in composition in such a way that the alloys are biocorrodible. Artificial plasma, as has been previously described according to EN ISO 10993-15:2000 for biocorrosion assays (composition NaCl 6.8 g/l, CaCl2 0.2 g/l, KCl 0.4 g/l, MgSO4 0.1 g/l, NaHCO3 2.2 g/l, Na2HPO4 0.126 g/l, NaH2PO4 0.026 g/l), is used as a testing medium for testing the corrosion behavior of an alloy under consideration. A sample of the alloy to be assayed is stored in a closed sample container with a defined quantity of the testing medium at 37° C. At time intervals, tailored to the corrosion behavior to be expected, of a few hours up to multiple months, the sample is removed and examined for corrosion traces according to techniques known to those skilled in the art. The artificial plasma according to EN ISO 10993-15:2000 corresponds to a medium similar to blood and thus represents a possibility for reproducibly simulating a physiological environment.

For purposes of the present disclosure, the term corrosion relates to the reaction of a metallic material with its environment, a measurable change of the material being caused, which, upon use of the material in a component, results in an impairment of the function of the component. For purposes of the present disclosure, a corrosion system comprises the corroding metallic material and a liquid corrosion medium, which simulates the conditions in a physiological environment in composition or is a physiological medium, particularly blood. On the material side, for example, factors, such as the composition and pretreatment of the alloy, microscopic and submicroscopic inhomogeneities, boundary zone properties, temperature and mechanical tension state, and, in particular, the composition of a layer covering the surface, influence the corrosion. On the side of the medium, for example, the corrosion process is influenced by conductivity, temperature, temperature gradients, acidity, volume-surface ratio, concentration difference, flow velocity, and the like.

For purposes of the present disclosure, implants, are devices introduced into the body via a surgical method and comprise fasteners for bones, such as screws, plates, or nails, surgical suture material, intestinal clamps, vascular clips, prostheses in the area of the hard and soft tissue, and anchoring elements for electrodes, in particular, of pacemakers or defibrillators.

The implant is preferably a stent. Stents of typical construction have a filigree support structure made of metallic struts which is initially provided in an unexpanded state for introduction into the body and is then widened into an expanded state at the location of application.

The x-ray marker is provided as a powder, preferably having a mean particle size less than or equal to 3 μm, the powder being embedded in the triglyceride acting as the organic carrier matrix. The advantage is, inter alia, in the simplification of the processing; a dispersion may be produced from the two components of the marker composite, possibly, but not necessarily, with a suitable solvent added, which may be applied to the implant via typical coating methods or may be used as a filler material for a cavity in the implant. After the degradation of the biocorrodible carrier matrix, the powdered marker component remains and is probably, but not necessarily, stored in extracellular vesicles because of the small particle size. It is to be assumed that an intercalation of the material of this type reduces the danger of inflammation or rejection reactions.

A second exemplary embodiment provides a medical implant having an x-ray marker corresponding to the above statements. In particular, the medical implant is a stent, preferably a stent made of the biocorrodible magnesium alloy.

Example 1

A stent made of the biocorrodible magnesium alloy WE43 (93 weight-percent magnesium, 4 weight-percent yttrium [W], and 3 weight-percent rare earth metal [E]) was coated with an x-ray marker as described below.

A suspension of 500 mg hydrogenated soybean oil (obtainable from Gustav Heess under the trade name Hydrogenated Soybean Oil Ph. Eur. 5.0, IP; fatty acid weight proportions: palmitic acid 9-16 weight-percent, stearic acid 79-89 weight-percent, oleic acid and isomers maximum 4 weight-percent, residual fatty acids each maximum 1 weight-percent), and 47.5 g TaC powder having a mean particle size of approximately 0.8-2 μm (obtainable from OSRAM SYLVANIA Products Inc.) was prepared with stirring and heated to a temperature of approximately 60° C. The hot suspension was dispersed in a cavity in the stent and subsequently cooled to room temperature.

All patents, patent applications and publications referred to herein are incorporated by reference in their entirety.

What is claimed is:

1. A marker composite for medical implants, the marker composite comprising:
   (a) 1-40 weight parts of a carrier matrix formed from at least one triglyceride having a melting point greater than or equal to 43° C., the carrier matrix comprising 90 weight-percent or more at least one triglyceride; and
   (b) 60-99 weight parts of a radiopaque marker component which is embedded in the carrier matrix,
   wherein the marker composite is suitable for use as a coating for a medical implant,
   wherein the medical implant is made of a biocorrodible metallic magnesium alloy material.

2. The marker composite of claim 1, wherein the carrier matrix comprises 90 weight-percent or more of a hydrogenated soybean oil having a proportion of palmitic acid in the fatty acids of the triglyceride in the range from 9-16 weight-percent and a proportion of stearic acid in the fatty acids of the triglyceride in the range from 79-89 weight-percent.

3. The marker composite of claim 1, wherein the marker component is a metal powder having a mean particle size less than or equal to 3 μm.

4. The marker composite of claim 3, wherein the metal powder is an element selected from the group consisting of Au, Ir, Pt, and Ta.

5. The marker composite of claim 1, wherein the carrier matrix further comprises tocopherol as an additive which lowers the viscosity.

6. A medical implant, coated and/or filled with a marker composite, comprising:
   (a) 1-40 weight parts of a carrier matrix having a melting point greater than or equal to 43° C., which comprises 90 weight-percent or more at least one triglyceride; and
   (b) 60-99 weight parts of a radiopaque marker component, which is embedded in the carrier matrix,
   wherein the medical implant is made of a biocorrodible metallic material.

7. A medical implant, coated and/or filled with a marker, comprising:
   (a) 1-40 weight parts of a carrier matrix having a melting point greater than or equal to 43° C., which comprises 90 weight-percent or more at least one triglyceride; and
   (b) 60-99 weight parts of a radiopaque marker component, which is embedded in the carrier matrix,
   wherein the medical implant is made of a biocorrodible magnesium alloy.

8. A medical implant, coated and/or filled with a marker composite, comprising:
   (a) 1-40 weight parts of a carrier matrix having a melting point greater than or equal to 43° C., which comprises 90 weight-percent or more at least one triglyceride; and
   (b) 60-99 weight parts of a radiopaque marker component, which is embedded in the carrier matrix;
   wherein the carrier matrix comprises 90 weight-percent or more of a hydrogenated soybean oil having a proportion of palmitic acid in the fatty acids of the hydrogenated soybean oil in the range from 9-16 weight-percent and a proportion of stearic acid in the fatty acids of the hydrogenated soybean oil in the range from 79-89 weight-percent,
   wherein the medical implant is made of a biocorrodible metallic material.

* * * * *